United States Patent
Zhao et al.

(10) Patent No.: US 8,865,971 B2
(45) Date of Patent: *Oct. 21, 2014

(54) METHODS OF TRANSFORMING SOMATIC CELLS OF MAIZE HAPLOID EMBRYOS

(71) Applicant: Pioneer Hi Bred International Inc, Johnston, IA (US)

(72) Inventors: Zuo-Yu Zhao, Johnston, IA (US); Dennis Bidney, Ankeny, IA (US); Evan Dale Elsing, Kauai, HI (US); William James Gordon-Kamm, Urbandale, IA (US); Michael D Miller, Winterset, IA (US); Xinli Wu, Johnston, IA (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/804,582

(22) Filed: Mar. 14, 2013

(65) Prior Publication Data

US 2013/0198893 A1 Aug. 1, 2013

Related U.S. Application Data

(63) Continuation of application No. 12/054,556, filed on Mar. 25, 2008, which is a continuation of application No. 10/121,200, filed on Apr. 12, 2002, now abandoned.

(60) Provisional application No. 60/285,265, filed on Apr. 20, 2001.

(51) Int. Cl.
*C12N 15/82* (2006.01)
*A01H 5/10* (2006.01)

(52) U.S. Cl.
CPC .......... *C12N 15/8241* (2013.01); *C12N 15/829* (2013.01); *C12N 15/8201* (2013.01); *A01H 5/10* (2013.01)
USPC ............ 800/294; 800/278; 800/288; 800/287

(58) Field of Classification Search
None
See application file for complete search history.

(56) References Cited

U.S. PATENT DOCUMENTS

| | | | | |
|---|---|---|---|---|
| 5,639,951 | A | 6/1997 | Bosemark et al. | 800/205 |
| 5,770,788 | A | 6/1998 | Jia | |
| 6,512,165 | B1 | 1/2003 | Ross et al. | 800/290 |
| 2008/0216198 | A1* | 9/2008 | Zhao et al. | 800/290 |

FOREIGN PATENT DOCUMENTS

| WO | WO 98/56811 | | 12/1998 | |
|---|---|---|---|---|
| WO | WO 99/61619 A2 | | 12/1999 | |
| WO | WO 00/50614 | * | 8/2000 | ............ C12N 15/82 |
| WO | WO 00/50614 A2 | | 8/2000 | |
| WO | WO 00/53784 | | 9/2000 | |
| WO | WO 01/31041 | | 5/2001 | |
| WO | WO 02/04649 A2 | | 1/2002 | |

OTHER PUBLICATIONS

Lowe et al. Use of maize LEC1 to improve transformation. (2000) In vitro cellular & developmental biology; abstract W-15 on p. 34-A.*
Niemirowicz-Szczytt, K. Excessive homozygosity in doubled haploids—advantages and disadvantages for plant breeding and fundamental research. (1997) Acta Physiologiae Plantarum; vol. 19; pp. 155-167.*
Lashermes et al. Genetic control of maternal haploidy in maize (*Zea mays* L.) and selection of haploid inducing lines. (1988) Theor. Appl. Genet.; vol. 76; pp. 405-410.*
Bonello et al. Esr genes show different levels of expression in the same region of maize endosperm. (2000) Gene; vol. 246; pp. 219-227.*
Welsh et al. Reporter gene expression for monitoring gene transfer. (1997) Current Opinion in Biotechnology; vol. 8; pp. 617-622.*
Alatortseva et al., "Reproduction of haploid and diploid maize forms in vitro", Maize Genet Coop Newsletter 75:56 (2001).
Chalyk et al., "Transgressive segregation in the progeny of a cross between two inducers of maize maternal haploids", Maize Genet Coop Newsletter 68:47 (1994).
Chalyk et al., "Regular segregation of four recessive marker genes among maternal haploids in maize", Plant Breeding 119:363-364 (2000).
Chalyk, S.T., "Creating new haploid-inducing lines of maize", Maize Genet Coop Newsletter 73:53-54 (1999).
Coe, E.H., Jr., "A Line of Maize with High Haploid Frequency", Am. Nat. 93:381-382 (1959).
Deimling et al., "Methodology and Genetics of in vivo Haploid Induction in Maize", Vortr. Pflanzenzuchtg 38:203-224 (1997) (in German with English Abstract).
Kato, A., "Single Fertilization in Maize" J Hered 90(2):276-280 (1999).
Kato, A., "Nitrous oxide (N2O) is effective in chromosome doubling of maize seedlings", Maize Genet Coop Newsletter 71:36-37 (1997).
Knox et al., "Dicamba and growth condition effects on doubled haploid production in durum wheat crossed with maize", Plant Breeding 119:289-298 (2000).
Lashermes et al., "Genetic control of maternal haploidy in maize (*Zea mays* L.) and selection of haploid inducing lines", Theor Appl Genet 76:405-410 (1988).
Lashermes et al., "Gynogenetic haploid plants analysis for agronomic and enzymatic markers in maize (*Zea mays* L.)", Theor Appl Genet 76:570-572 (1988).

(Continued)

*Primary Examiner* — Cathy Kingdon Worley

(57) ABSTRACT

Methods for producing homozygous plants, seeds, and plant cells are provided. The methods comprise transforming a somatic cell of a maize haploid embryo with a polynucleotide of interest and treating the transformed cell with a chromosome doubling agent. One or more growth stimulation proteins, such as, for example, RepA or Lec1, may also be provided.

8 Claims, No Drawings

(56) References Cited

OTHER PUBLICATIONS

Mehta et al., "Somaclonal variation for disease resistance in wheat and production of dihaploids through wheat x maize hybrids", *Genetics and Molecular Biology* 23(3):617-622 (2000).

Tahir et al., "Production of Haploid Plants in Crosses between F1-Generation of Wheat with Maize", *Pak J Sci Ind Res* 43(4):258-261 (2000).

Gordon-Kamm et. al., Stimulation of the cell cycle and maize transformation by disruption of the plant retinoblastoma pathway, PNAS 99(18):11975-11980 (Sep. 2002).

Hellens et al., pGreen: a versatile and flexible binary Ti vector for *Agrobacterium*-mediated plant transformation, Plant Molecular Biology 42:819-832 (2000).

Nikovics et al., Cell-Cycle, Phase-Specific Activation of Maize streak virus Promoters, MPMI 14(5):609-617 (May 2001).

Qin et al., Construction of a Shuttle Vector and Transformation of *Xylella fastidiosa* with Plasmid DNA, Current Microbiology 43:158-162 (Sep. 2001).

Iida et al., Efficiency of Particle-Bombardment-Mediated Transformation Is Influenced by Cell Cycle Stage in Synchronized Cultured Cells of Tobacco, Plant Physiol. (1991) 97:1585-1587.

Okada et al., Expression and integration of genes introduced into highly synchronized plant protoplasts, Mol. Gen. Genet. (1986) 205:398-403.

Stoger et al., Plant transformation by particle bombardment of embryogenic pollen, Plant Cell Reports (1995) 14:273-278.

Martin and Widholm. 1996. Plant Cell Reports. vol. 15. p. 781-785.

Phillips et al. Proc. Natl. Acad. Sci USA vol. 91, p. 5222-5226. 1994.

Leitch and Bennett. Trends in plant science. vol. 2(12). 1997.

Swanson et al., Theor. Appl. Gnet., 1989, vol. 78, pp. 831-835.

Gayen et al., Maize Newsletter, 1994, vol. 68, p. 65.

Rosari et al., Crop Sci., 1994, vol. 34, pp. 343-347.

Sarker et al., Genetics, 1966, vol. 54, pp. 453-464.

Liu. Maize Genetics Cooperation Newsletter 71: 41, 1997.

Barnabas et al. Plant Cell Reports 18: 858-862, 1999.

J. Eder et al., In vivo haploid induction in maize, Theor Appl Genet (2002) 104:703-708.

L. E. Aulinger et al., Rapid attainment of a doubled haploid line from transgenic maize (*Zea mays* L.) plant by means of another culture, In Vitro Cell Dev. Biol-Plant, Mar.-Apr. 2003, 39:165-170, 14:273-378.

Welsh et al., Reporter gene expression for monitoring gene transfer, (1997), Current Opinion Biotechnology, vol. 8; pp. 617-622.

Lowe et al., Use of maize LEC1 to improve transformation, In vitro cellular & developmental biology, (2000), abstract W-15 on p. 34-A.

Yie et al., Rapid production and field testing of homozygous transgenic tobacco lines with virus resistance conferred by expression of satellite RNA and coat protein of cucumber mosaic virus, Transgenic Research, (1995), vol. 4, pp. 256-263.

Niemirowicz-Szczytt, K., Excessive homozygosity in doubled haploids—advantages and disadvantages for plant breeding and fundamental research, Acta Physiologiae Plantarum, (1997) vol. 19, pp. 155-167.

Lashermes et al., Genetic control of maternal haploidy in maize (*Zea mays* L) and selection of haploid inducing lines, Theor Appl Genet, (1998), vol. 76, pp. 405-410.

Bonello et al., Esr genes show different levels of expression in the same region of maize endosperm, Gene, (2000), vol. 246, pp. 219-227.

William Gordon-Kamm et al., Stimulation of the cell cycle and maize transformation by disruption of the plant retinoblastoma pathway, PNAS, Sep. 3, 2002, vol. 99, No. 18, pp. 11975-11980.

Ashok Kumar Shrawat et al., *Agrobacterium*-mediated transformation of cereals: a promising approach crossing barriers barriers, Plant Biotechnology Journal, 2006, vol. 4, pp. 575-603.

* cited by examiner

METHODS OF TRANSFORMING SOMATIC CELLS OF MAIZE HAPLOID EMBRYOS

CROSS-REFERENCE TO RELATED APPLICATIONS

This application is a continuation of U.S. Ser. No. 12/054,556 filed Mar. 15, 2008 and now pending, which is a continuation of U.S. Ser. No. 10/121,200 filed Apr. 12, 2002 and now abandoned, which claims priority to U.S. Ser. No. 60/285,265 filed Apr. 20, 2001, the disclosures of which are incorporated herein by reference.

FIELD OF THE INVENTION

The present invention relates to the field of genetic engineering of plants and to methods for introducing traits into plants,

BACKGROUND OF THE INVENTION

Many current transformation technologies produce mainly heterozygous transgenic plants. However, homozygous transgenic plants are basic for product development and commercialization of plants. To obtain homozygous transgenic plants requires several generations of self-pollination and segregation analysis. This is an inefficient use of labor and lime resources. It would therefore be useful to develop a method to reduce hand pollination steps normally required to obtain a homozygous transgenic plant.

DETAILED DESCRIPTION OF THE INVENTION

As used herein "Growth Stimulation Polynucleotides" include polynucleotides whose encoded products stimulate growth either through triggering developmental programs (i.e. embryogenesis, meristem formation, meristem maintenance, etc) or through stimulating the cell cycle.

As used herein "Transformation" includes stable transformation and transient transformation unless indicated otherwise.

As used herein "Stable Transformation" refers to the transfer of a nucleic-acid fragment into a genome of a host organism (this includes both nuclear and organelle genomes) resulting in genetically stable inheritance. In addition to traditional methods, stable transformation includes the alteration of gene expression by any means including chimerplasty or transposon insertion.

As used herein "Transient Transformation" refers to the transfer of a nucleic acid fragment or protein into the nucleus (or DMA-containing organelle) of a host organism resulting in gene expression without integration and stable inheritance.

As used herein, "nucleic acid" includes deoxyribonucleotide or ribonucleotide polymer, or chimeras thereof, in either single- or double-stranded form, and unless otherwise limited, encompasses known analogues having the nature of natural nucleotides in that they hybridize to single-stranded nucleic acids in a manner similar to naturally occurring nucleotides (e.g., peptide nucleic acids).

As used herein, the term "plant" includes reference to whole plants, plant organs (e.g., leaves, sterns, roots, etc.), seeds and plant cells and progeny of same, "Plant cell", as used herein includes, without limitation, seeds, suspension cultures, embryos, meristematic regions, callus tissue, leaves, roofs, shoots, gametophytes, sporophytes, pollen, and microspores. The class of plants which can be used in the methods Of the invention include both monocotyledonous and dicotyledonous plants.

Methods for obtaining homozygous plants, plant cells, and seeds are provided. Also provided are methods for obtaining haploid embryos and seeds and methods for increasing chromosomal doubling. The methods comprise contacting haploid ceils with a chromosome doubling agent and providing a growth stimulation protein. The methods also comprise crossing a selected plant and an inducer line to produce haploid embryos or seeds while providing a growth stimulation polynucleotide. Other methods comprise crossing a selected plant and an inducer tine to produce a haploid cell, providing a growth stimulation polynucleotide, and treating the haploid cell with a chromosome doubling agent. Also provided are methods for producing transgenic homozygous plants and seeds. The methods comprise transforming a cell torn haploid somatic tissue such as embryo, meristem, leaf, root, inflorescence, callus tissue derived from such tissue, or seed and then contacting the transformed cell with a chromosome doubling agent. The methods provide homozygous plant cells which can be regenerated into a plant containing homozygous genes. The methods avoid time consuming crossing methods to obtain a homozygous trait of interest, The methods can be useful for functional genomics, such as knock-out analysis, functional analysis of recessive genes, gene replacement, gene targeting, transgene stacking, and evaluating lethal versus non-lethal analysis of genes. With the current diploid transformation system, these analyses are very complicated and costly. The inventive methods can be used to transform and express recessive genes in T0 plants.

Haploid induction systems have been developed tor various plants to produce haploid tissues, plants and seeds. The haploid induction system can produce haploid plants from any genotype by crossing a selected line (as female) with an inducer line. Such inducer lines for maize include Stock 8 (Coe, 1959, *Am, Nat* 93:381-382; Sharkar and Coe, 1986, *Genetics* 54:453-464) RWS (Roeber and Geiger 2001, submitted to Crop Science), KEMS (Deimling, Roeher, and Geiger, 1997, *Vortr. Pflsnzenzuchtg* 38:203-224), or KMS and ZfVIS (Chalyk, Bylich & Chebotar, 1994, *MNL* 68:47; Chalyk & Chebotar, 2000, *Plant Breeding* 119:363-364), and indeterminate gametophyte (ig) mutation (Kermicle 1989 *Science* 186:1422-1424). The disclosures of which are incorporated herein by reference.

Methods for obtaining haploid plants are also disclosed in Kohayashi, M. et al., *Journ. of Heredity* 71(1 ):9-14,1980, Pollacsek, M., Agronomie (Paris) 12(3):247-251,1992; Cho-Un-Haing et ah, *Journ. of Plant Biol.,* 1996, 39(3):185-188; Verdoodt, L.f et al., Feb. 1998, 96(2):294-300; Genetic Manipulation in Plant Breeding, Proceedings international Symposium Organized by EUCARPIA, Sep. 8-13, 1985, Berlin, Germany; Chalyk et al., 1994, Maize Genet Coop. Newsletter 68:47; Chalyk, S. T., 1999, *Maize Genet Coop. Newsletter* 73:53-54; Coe, R. H., 1959, *Am. Nat.* 93:381-382; Deimling, S. et al., 1997, *Vortr. Pflanzenzuchtg* 38:203-204; Kato, A., 1999, *J. Hered.* 90:276-280; Lashermes, P, et al., 1988, *Theor. Appl. Genet.* 76:570-572 and 76:405-410.; Tymov, V. S. et al, 1984, Dokl. Akad. Nauk. SSSR 276:735-738; Zabirova, E. R. et al., 1996, Kukuruza I Sorgo N4, 17-19: Aman, M. A., 1978, *Indian J. Genet Plant Breed* 38:452-457; Chalyk S. T., 1994, *Euphytica* 79:13-18; Chase, S. S., 1952, *Agron. J.* 44:263-287; Coe, E. H., 1959, *Am. Nat.* 93:381-382; Coe, E. H., and Sarkar, K. R., 1964 *J, Hered.* 55:231-233; Greenblatt, I. M. and Bock, M., 1967, *J. Hered,* 58:9-13; Kato, A., 1990, *Maize Genet. Coop, Newsletter* 65:109-110; Kato, A., 1997, *Sex. Plant Reprod.* 10:96-100; Nanda, D. K.

and Chase, S. S., 1966, *Crop Sci.* 6:213-215; Sarkar, K. R. and Coe, E. H., 1996, *Genetics* 54:453-464; Sarkar, K. R, and Coe, E. H., 1971, *Crop Sci.* 11:643-544; Sarkar, K. R. and Sachan J. K S., 1972, *Indian J. Agric. Sci.* 42:781-786; Kermicle J. L., 1969, Merita Yeshwant, M. R., Genetics and Molecular Biology. September 2000, 23(3):617-622; Tahir, M. S. et al. Pakistan Journal of Scientific and Industrial Research, August 2000, 43(4):258-261; Knox, R. E. et al. Plant Breeding, August 2000, 119(4):280-208; and U.S. Pat. No. 5,639,951 the disclosures of which are incorporate herein by reference.

Somatic haploid cells, haploid embryos, haploid seeds, or haploid seedlings produced from haploid seeds can be treated with a chromosome doubling agent. Homozygous plants can be regenerated from haploid cells by contacting the haploid cells, such as embryo cells or callus produced from such cells, with chromosome doubling agents, such as colchicine, anti-microtubule herbicides, or nitrous oxide to create homozygous doubled haploid cells. Treatment of a haploid seed or the resulting seedling generally produces a chimeric plant, partially haploid and partially doubled haploid, it may be beneficial to nick the seedling before treatment With colchicine. When reproductive tissue contains doubled haploid cells, then doubled haploid seed is produced.

Haploid embryos, haploid seeds, or somatic haploid cells from a haploid plant can be harvested and transformed by any known means. Transgenic homozygous plants can be regenerated from the transformed ceils as described above. Transgenic homozygous seeds can also be produced by the method described above by treating a haploid seed or the resulting seedling with a chromosome doubling agent and growing the seed to produce a plant having homozygous seeds.

Methods of chromosome doubling are disclosed in Antoine-Michard, S. et al., Plant cell, tissue organ cult., Cordrecht, the Netherlands, Kluwer Academic Publishers, 1997, 48(3): 203-207; Kato, A., Maize Genetics Cooperation Newsletter 1997, 38-37; and Wan, Y. et al., TAG, 1989, 77:889-892, Wan, Y. et al., TAG, 1991, 81:205-211. The disclosures of which are incorporated herein by reference. Typical methods involve contacting the transformed cell with nitrous oxide, anti-microtubule herbicides, or colchicine, Polynucleotides or polypeptides involved in growth stimulation or cell cycle stimulation can be used to increase the frequency of haploid embryos produced per ear, increase the recovery of transformed haploid plants, and/or stimulate chromosomal doubling efficiency. The growth stimulation polynucleotide can be provided by either the female or male parent. The growth stimulation polynucleotide or polypeptide can be provided by stable or transient transformation.

Polynucleotides whose overexpression has been shown to stimulate the cell cycle include Cyclin A, Cyclin B, Cyclin C, Cyclin D, Cyclin E, Cyclin F, Cyclin G, and Cyclin H; Pin1; E2F; Cdc25; RepA and similar plant viral polynucleotides encoding replication-associated proteins. In addition, there are other cell cycle regulatory polynucleotides whose expression must be down-regulated to stimulate the cycle and concomitant cell division. These include polynucleotides whose encoded polypeptides normally repress the cell cycle, such as Rb, CKl, prohibitin, and wee1. Thus, polynucleotides that encode polypeptides involved in the regulation of the cell cycle in plants can be used in the invention, and include eyelins (Doerner (1994) Plant Physiol. 106:823-827.), maize cdc2 (Colasanti et al. (1991) PNAS 88:3377-3381 ), other cdc2 WO 99/53069, cdc25+ (Russell and Nurse (1986) Cell 45:145-153), the geminivirus RepA gene (U.S. Ser. No. 09/257,131), plant E2F (Ramirez-Parra et al. (1999) Nuc. Ac. Res. 27:3527-3533 and Sekine et al. (1999) FEBS Lett. 460: 117-122), Pin1 (Liou et al., 2002, Proc Natl Acad Sci USA 99(3):1335-40 and Yso et al, 2001, J Biol Chem 276(17): 13517-23), Cyclin D disclosed in WO 00/17354 published Mar. 30, 2000, CKS polynucleotides disclosed in 99/61619 filed May 19, 1999, Cyclin E polynucleotides disclosed in 09/496,444 fried Feb. 2, 2000. Repressors of the cell cycle such as Rb (Grafi et al. (1996) Proc Natl Acad Sci 93(17): 8962-7; Ach et al. (1997) Mol Cell Biol 17(9):5077-86), CKI (U.S. Ser. No. 01/44038 filed Nov. 6, 2001), prohibitin (WO 00/15818), and wee1 (disclosed in WO 00/37645) genes can be used in the practice of the invention. The disclosures of which are herein incorporated by reference.

Examples of plant virus replicase polynucleotide sources suitable for growth stimulation (i.e. stimulation of S-phase in the cell cycle) include wheat dwarf virus, maize streak virus, tobacco yellow dwarf virus, tomato golden mosaic virus, abutllon mosaic virus, cassava mosaic virus, beet curly top virus, bean dwarf mosaic virus, bean golden mosaic virus, chiohs striate mosaic virus, digitaria streak virus, miscanthus streak virus, maize streak virus, panicum streak virus, potato yellow mosaic virus, squash leaf curl virus, sugarcane streak virus, tomato golden mosaic virus, tomato leaf curl virus, tomato mottle virus, tobacco yellow dwarf virus, tomato yellow leaf curl virus, African cassava mosaic virus, and the bean yellow dwarf virus. Replicase from the wheat dwarf virus has been sequenced and functionally characterized. Replicase binds to a well-characterized binding motif on the Rb protein (Xie et al., *The EMBO Journal* Vol. 14 no, 16 pp. 4073-4082, 1995; Orozco et al., *Journal of Biological Chemistry,* Vol, 272, No. 15, pp. 9840-9846, 1997; Timmermans et al., *Annual Review Plant Physiology. Plant Mol. Biol,* 45:79-112, 1994; Stanley, Genetics and Development 3:91-96, 1996; Davies et al., *Geminvirus Genomes*, Chapter 2, and Gutierrez, Plant Biology 1:492-497, 1998). Other growth stimulation (S-phase stimulating) polynucleotides suitable for use include viral cell cycle modulator proteins such as CLINK (Aronson et al *Journal of Virology* 74:2968-2972, 2000). Examples of other viral sources for this type of protein include banana bunchy top virus, milk vetch dwarf virus, subterranean clover stunt virus Ageratum yellow vein virus and other representatives of plant nanoviruses. The disclosures of these items are incorporated herein by reference.

Growth stimulation polynucleotides include polynucleotides whose overexpression stimulates growth through triggering developmental programs include such examples as SERK, Lec1, Lec2, WUS, FUS3, ABI3 (Vp1), BMN3, ANT, and members of the Knotted family, such as Kn1, STM, OSH1, and SbH1; cytokinin genes such as IPT, TZS, CKI-1; and genes that produce growth stimulating peptides such as PSK. Also, genes whose encoded products repress specific plant developmental programs can be down-regulated to stimulate growth, such as the gene PICKLE, that when down-regulated results in embryogenic growth. Thus, these genes useful in the present invention include the Kn1 family of genes disclosed in Vollbrecht et al., *Nature* 350:241-243, 1991; Sentoku et al. *Develop. Biol.* 220:358-364, 2000 and Sinha et al., 1993, *Genes Dev* 7(5):787-96, WUSCHEL or WUS genes found in Mayer et al., *Cell* 95:805-815, 1998; Lenhard et al., *Cell* 105(6):805-14; and Laux et al, 1996, *Development* 122(1):87-96, Lec1 polynucleotides disclosed in U.S. Ser. No. 99/26514 filed Nov. 9, 1999, SERK polynucleotides disclosed in Schmidt et al. 1997, *Development* 124(10):2049-62 and Baudino et al. 2001, Planta 213(1):1-10, Babyboom (BMN3) polynucleotides disclosed in EP1057891 (A1), LEC2 polynucleotides disclosed in Stone et al. 2001, *Proc Natl Acad Sci U S A* 98(20):11806-11, FUS3 polynucleotides disclosed in Nambara et al, 2000, *Dev Biol*

220(2):412-23 and Violent et al., 2000, *J Exp Bot* 51 (347): 995-1003, STM polynucleotides disclosed in Endrizzi el al. 1996, *Plant J*10(6):967-79 and Long et al. 1996, *Nature* 379): 66-9.8, ANT (Ainteguinent) polynucleotides disclosed in Mizukami, 2001, *Curr Opin Plant Biol* 4(6):533-9; Nole-Wilson S, Krizek BA., 2000, *Nucleic Acids Res* 28(21):4076-82; Mizukami Y, Fischer RL., 2000, *Proc Natl Acad Sci USA* 97(2); 942-7; and Krizek BA., 1999, *Dev Genet* 25(3):224-36, ABI3 polynucleotides disclosed in Suzuki et al. 2001, *Plant J* 28(4):409-18; Rohde et al., 2000, *Trends Plant Sci* 5(10):418-9; Percy et al., 1997, *Plant Cell* 9(8):1265-77; Parcy F, Giraudat J., 1997, *Plant J* 11(4):693-702, and PICKLE (Ogas et al., PNAS 96:13839-13844, 1999). Genes that stimulate growth by encoding products involved in the synthesis of growth stimulating hormones (IPT, TZS), that confer independence from a hormone (CKI1) or in which the peptide itself is a growth stimulating hormone (PSK). Thus, such genes can fee used in the present invention and include the IPX gene of Agrobacterium tumefaciens (Strabala et al. (1989) *Mol. Gen. Genet.* 216:338-394, Bonnard et al. (1989) *Mol Gen. Genet.* 216:428-438, DPBJ/EMBt/GenSank), TZS (Beaty et al. (1986) *Mol. Gen. Genet.* 203:274-280, Akiyoshi et al. (1985) *Nucleic Acids Res.* 13:2773-2738, Regier et al. (1989) *Nucleic Acids Res.* 17:8885), CKI1 (Kakimoto (1996) *Science* 274:932-985), and PSKα (Yang et al. (1999) PNAS 96:13580-13586). The disclosures of the above are incorporated herein by reference.

As discussed above, growth stimulation polynucleotides (or polypeptides) can be used to increase chromosomal doubling in haploid plant tissues (callus, seeds, seedlings etc,) with the methods described herein. Xhe frequency of doubled haploids can be increased several fold. The growth stimulation polynucleotides can be introduced into the male or female parent. Introducing the growth stimulation polynucleotides into the maternal parent will result in a plant homozygous for the growth stimulation polynucleotide, if the growth stimulation polynucleotide is introduced into the paternal parent (the inducer line) the growth stimulation polynucleotide would be present in the endosperm, but not in the embryo. This can result in increased vigor of the haploid embryo.

After successful doubling of the haploid chromosomes, it may be desirable to remove the above growth stimulation polynucleotides. This can be accomplished by using various methods of gene excision, such as those described below including the use of recombination sites and recombinases.

In another aspect the inducer line may contain a scorable marker gene, for example colored markers in the endosperm, embryo or stem. Such markers include GUS (U.S. Pat. Nos. 5,599,870 and 5,432,081), GFP (U.S. Pat. Nos. 6,146,826; 5,491,084; and WO 97/41228), luciferase (U.S. Pat. No. 5,674,713 and Ow et al 1986 *Science* 234 (4778) 856-859), CRC (Ludwig et al., 1990) other anthooyanln genes such as A, C, R-nj, etc, and others known in the art. The disclosures of which are incorporated herein by reference. When the inducer line is crossed with the selected line, the resulting haploid seeds will have colored endosperm with colorless embryo. Some lines already contain a color marker. For various reasons it may be desirable to express the marker gene in the embryo. In particular, it may be desirable to express the marker gene in the early stage of development, about 8-15 days after pollination using an appropriate promoter such as an oleosin or a Lec1 promoter. Marker negative embryos are then selected to obtain haploid embryos. This method provides the advantage of obtaining haploid embryos without marker genes.

The methods of the invention can be practiced with any plant. Such plants include but are not limited to maize, soybean, oilseed *Brassica*, alfalfa, rice, rye, sorghum, sunflower, tobacco, potato, peanuts, cotton, sweet potato, cassava, sugar beets, tomato, oats, barley, and wheat.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increases, the choice of genes for transformation will change accordingly. It is also understood that two or more genes may be introduced into a plant.

General categories of genes of interest include for example, those genes involved in information, such as zinc fingers, those involved in communication, such as kinases, and those involved in housekeeping, such as heat shock proteins. More specific categories of transgenes, for example, include genes encoding agronomic trails, insect resistance, disease resistance, herbicide resistance, sterility, grain characteristics, and commercial products. Genes of interest also include those involved in oil, starch, carbohydrate, or nutrient metabolism as well as those affecting for example kernel size, sucrose loading, and the like. The qualify of grain is reflected in traits such as levels and types of oils, saturated and unsaturated, quality and quantity of essential amino acids, and levels of cellulose.

Grain traits such as oil, starch, and protein content can be genetically altered,. Modifications include increasing the content of oleic acid, saturated or unsaturated oils, increasing levels of lysine and sulfur, providing essential amino acids, and also modification of starch. Hordothlonin protein modifications are described in U.S. Pat. No. 5,990,389 issued Nov. 23, 1999, U.S. Pat. No. 5,885,801 issued Mar. 23, 1999, U.S. Pat. No. 5,885,802 issued Mar. 23, 1999 and U.S. Pat. No. 5,703,409. Another example is lysine and/or sulfur rich seed protein encoded by the soybean 2S albumin described in U.S. Pat. No. 5,850,016 issued Dec. 15, 1998, and the chymotrypsin inhibitor from barley, Williamson et al, (1987) *Eur. J. Biochem.* 185:99-106. The disclosures of the above are herein incorporated by reference.

Derivatives of the coding sequences can be made by site-directed mutagenesis, to increase the level of preselected amino acids in the encoded polypeptide. For example, the gene encoding the barley high lysine polypeptide (BHL) is derived from barley chymotrypsin inhibitor WO98/20133 the disclosure of which is incorporated herein by reference. Other proteins include methionine-rich plant proteins such as from corn (Pedersen et al, (1986) *J. Biol Chem.* 261:6279; Kirihara et al. (1988) *Gene* 71:359; and rice (Musumura et al (1989) *Plant Mol. Biol.* 12:123), The disclosures of which are incorporated herein by reference. Other genes encode latex, Floury 2, growth factors, seed storage factors, and transcription factors.

Insect resistance genes may encode resistance to pests that have great yield drag such as rootworm, cutworm, European Corn Borer, and the like. Such genes include, for example *Bacillus thuringiensis* toxic protein genes (U.S. Pat. Nos. 5,386,892; 5,747,450; 5,737,514; 5,723,756; 5,593,881; Geiser et al. (1986) *Gene* 48:109); lectins (Van Damme et al. (1994) *Plant Mol. Biol.* 24:825); and the like. Genes encoding disease resistance traits include detoxification genes, such as against fumonisin (U.S. Pat. No. 5,792,931, issued Aug. 11, 1998); avirulence (avr) and disease resistance genes (Jones et al. (1994) *Science* 286:789; Martin et al. (1993) *Science* 262: 1432; Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the 84 and/or Hra mutations), genes coding for resistance to herbicides that act to inhibit action of glutamine synthase, such as phosphinothricin or baste (e.g., the bar gene), or other such genes known in the art. The bar gene encodes resistance to the herbicide basta, the nptll gene encodes resistance to the antibiotics kanamycin and geneticin, and the ALS gene encodes resistance to the herbicide chlorsulfuron. Glyphosate tolerance can be obtained from the EPSPS gene.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could increase for example, starch for ethanoi production, or provide expression of proteins. Another commercial use of transformed plants is the production of polymers and bioplastics such as described in U.S. Pat. No. 5,802,321 issued Feb. 11, 1997. Genes such as B-Ketothiolase, PHBase (polyhydroxybutyrate synthase) and acetoacetyl-CoA reductase (see Schubert et al. (1988) *J. Bacteriol.* 170:5837-5847) facilitate expression of polyhyroxyaikanoates (PHAs). Genes of medicinal and pharmaceutical uses, such as that encoding avidin and vaccines or proteins produced utilizing plants as factories are also contemplated as part of this invention.

It is recognized that the present invention contemplates the use of various gene targeting methods. Insertion, excision or recombination sites for use in the invention are known in the art and include FRT or Iox sites (see, for example, Sehlake et al. (1994) *Biochemistry* 33:12748-12751; Huang et al. (1991) *Nucleic Acids Res.* 19:443-448; Sadowski (1995) *Prog. Nuc. Acid Res. Mol. Bio.* 51:53-91; Cox (1989) *Mobile DNA*, ed. Berg and Howe (American Society of Microbiology, Wash. D.C.), pp. 116-670; Dixon et al. (1995) 18:449-458; Umlauf et al. (1988) *EMBO J.* 7:1845-1852; Buchholz et al. (1996) *Nucleic Acids Res.* 24:3118-3119; Kilby et al, (1993) *Trends Genet.* 9:413-421; Roseanne et al. (1995) *Nat Mad.* 1:592-594; Albert et al. (1995) *Plant J.* 7:649-659; Bailey et al. (1992) *Plant Mol. Biol.* 18:353-361; Odell el al. (1990) *Mol. Gen. Genet.* 223:369-378; and Dale et al. (1991) *Proc. Natl. Acad. Sci. USA* 88:10558-105620; Iox (Albert et al. (1995) *Plant J.* 7:649-659; Qui et al, (1994) *Proc. Natl. Acad. Sci. USA* 91:1706-1710; Stuurman et al. (1996) *Plant Mol. Biol.* 32:901-913; Odell et al. (1990) *Mol. Gen. Genet.* 223:369-378; Dale et al. (1990) *Gene,* 91:79-85; and Bayley et al. (1992) *Plant Mol. Biol.* 18:353-361); U.S. Pat. Nos. 5,658, 772; 4,959,317; 6,110,736. Such recombination sites in the presence of a compatible recomhinase allow for the targeted integration of one or more nucleotide sequences of interest into the plant genome. It is recognized that variations of targeted insertion can also be practiced with the invention. See for example WO 99/25821; WO 99/25355; WO 99/25340; WO 99/25853. The disclosures of the above are herein incorporated by reference.

Where appropriate, the nucleotide sequences of interest may he optimized for increased expression in the plant. Where mammalian, yeast, or bacterial genes are used in the invention, they can be synthesized using plant-preferred codons for improved expression, it is recognized that for expression in monocois, dicot genes can also be synthesized using monocot-preferred codons. Methods are available in the art for synthesizing plant-preferred genes. See., for example, U.S. Pat. Nos. 5,380,831, 5,430,391, and Murray et al, (1989) *Nucleic Acids Res.* 17:477-498, herein incorporated by reference.

The plant-preferred codons may be determined from the codons utilized more frequently in the proteins expressed in the recipient plant of interest. It is recognized that monocot-or dicot-preferred sequences may be constructed as well as plant-preferred sequences for particular plant species. See, for example, EPA 0359472; EPA 0385962; WO 91/16432; Periak et al. (1991) *Proc. Natl. Acad. Sci. USA* 88:3324-3328; and Murray et al. (1989) *Nucleic Acids Res.* 17:477-498; U.S. Pat. Nos. 5,380,831 and 5,436,391; and the like, herein Incorporated by reference. It is further recognized that all or any part of the gene sequence may be optimized or synthetic. That is, fully optimized or partially optimized sequences may also be used.

Additional sequence modifications are known to enhance gene expression in a cellular host and can be used in the invention. These include elimination of sequences encoding spurious polyadenyiation signals, exon-intron splice site signals, transposon-like repeats, and other such well-characterized sequences, which may be deleterious to gene expression. The G-C content of the sequence may be adjusted to levels average for a given cellular host, as calculated by reference to known genes expressed in the host celt When possible, the sequence may be modified to avoid predicted hairpin secondary mRNA structures.

In one example, where a DNA construct comprising a compatible recombinase gene is to be used for targeted integration of a nucleotide sequence of interest into a target site within a chromosome of interest, the nucleotide sequence encoding the compatible recombinase may be constructed with plant-preferred codons. More particularly, where the gene encodes a PtP recombinase, for example, the FLP gene sequence may be constructed using plant-preferred codons to obtain an FLP recombinase that is optimized for expression in the plant, WO 99/27077, the disclosure of which is incorporated herein by reference.

The nucleotide sequences of interest may be utilized in an expression cassette. Generally the nucleotide sequence of interest is operably linked with a functional promoter, and in most instances a termination region. There are various ways to achieve the expression cassette within the practice of the invention. In one embodiment of the invention, the nucleotide sequence of interest is transferred or inserted into the genome as an expression cassette. Alternatively, the nucleotide sequence may be inserted into a site within the genome that is 3' to a promoter region. In this latter instance, the insertion of the coding sequence 3' to the promoter region is such that a functional expression cassette is achieved upon integration.

For convenience, the nucleotide sequences of interest are generally provided in expression cassettes for expression in the plant. The cassette will include 5' and 3' regulatory sequences operably linked to a nucleotide sequence of interest. By "operably linked" is intended a functional linkage between a promoter and a second sequence, wherein the promoter sequence initiates and mediates transcription of the nucleic acid sequence corresponding to me second sequence. The cassette may additionally contain at least one additional gene or nucleotide sequence of interest to be cotransformed into the plant. Thus, each nucleic acid sequence will be operably linked to 5' and 3" regulatory sequences. Alternatively, the additional gene(s) or nucleotide sequencers) can be provided on multiple expression cassettes.

The construction of such expression cassettes which can be employed in conjunction with the present invention is well known to those of skill in the art in light of the present disclosure. See, e.g., Sambrook et al., *Molecular Cloning: A Laboratory Manual*; Cold Spring Harbor, New York: (1939): Gelvin et al., *Plant Molecular Biology Manual* (1990); *Plant Biotechnology: Commercial Prospects and Problems*, eds. Prakash et al., Oxford & IBH Publishing Co.; New Delhi, India; (1993); and Heslot et al., *Molecular Biology and Genetic Engineering of Yeasts*; CRC Press, Inc., USA; (1992); each disclosure incorporated herein by reference.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal. Such an expression cassette is generally provided with a plurality of restriction sites for insertion of the nucleotide sequence of interest that is to be under the transcriptional regulation of the regulatory regions.

The expression cassette may additionally contain selectable marker genes. The marker gene confers a selectable phenotype on plant cells. Usually, the selectable marker gene will encode antibiotic or herbicide resistance. Suitable genes include those coding for resistance to the antibiotics spectinomycin and streptomycin (e.g., the acid gene), the streptomycin phosphotransferase (SPT)gene coding for streptomycin resistance, the neomycin phosphotransferase (NPTH) gene encoding kanamycin or geneticin resistance, the hygromycin phosphotransferase (HPT) gene coding for hygromycin resistance.

Suitable genes coding for resistance to herbicides include those which act to inhibit the action of acetoiaetate synthase (ALS), in particular the sulfonylurea-type herbicides (e.g., the acetoiaetate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Selectable marker genes for the selection of transformed cells or tissues are disclosed in the following publications. See generally, Yarranton (1992) *Curr. Opin. Biotech.* 3:506-511; Christopherson et al. (1992) *Proc. Natl. Acad Sci. USA* 89:6314-6318; Yao et al. (1992) *Cell* 71:63-72; Reznikoff (1992) *Mol. Microbiol.* 8:2419-2422; Barkley et al. (1930) *Operon*, pp. 177-220; Hu et al. (1987) *Cell* 48:555-566; Brown et al. (1987) *Cell* 49:803-812; Figge et al. (1988) *Cell* 52:713-722; Deuschle et al. (1989) *Proc. Natl. Acad. Sci. USA* 86:5400-5404; Fuerst et al, (1989) *Proc. Natl. Acad. Sci. USA* 86:2549-2553; Deuschle et al. (1990) *Science* 248:480-483; M. Gossen (1993) Ph.D dissertation, University of Heidelberg; Raines et al. (1993) *Proc. Natl. Acad. Sci USA* 90:1917-1921; Labow et al. (1990) *Mol. Cell Bio.* 10:3343-3356; Zambretti et al. (1992) *Proc. Natl. Acad. Sci. USA* 89:3952-3956; Baim et al. (1991) *Proc. Natl. Acad. Sci. USA* 88:5072-5078; Wyborski et al. (1991) *Nucleic Acids Res.* 19:4867-4653; Hillenand-Wissman (1989) *Topics in Mol. and Struc. Biol.* 10:143-162; Degenkolb et al. (1991) *Antimicrob. Agents Chemother* 35:1591-1595; Kleinschnidt et al. (1988) *Biochemistry* 27:1094-1104; Gatz et al. (1992) *Plant J.* 2:397-404; A. L. Bonin (1993) Ph.D, dissertation, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Exp. Pharmacology* 78; Gill et al. (1988) *Nature* 334:721-724, Such disclosures are herein Incorporated by reference.

The expression cassette will generally include in the 5'-3' direction of transcription, a transcriptional and translational initiation region, a nucleotide sequence of interest and a transcriptional and translational termination region functional in plants. The transcriptional initiation region, the promoter, may be native or analogous or foreign or heterologous to the plant host. Additionally, the promoter may fee the natural sequence or alternatively a synthetic sequence. By "foreign" is intended that the transcriptional initiation region is not found in the native plant info which the transcriptional initiation region is introduced.

While it may be preferable to express the nucleotide sequences of interest using heterologous promoters, the native promoter sequences may be used, Such constructs would change expression levels of any protein encoded by a nucleotide sequence of interest in the plant or plant cell. Thus, the phenotype of the plant or plant cell is altered.

Constitutive, tissue-preferred or inducible promoters can foe employed. Examples of constitutive promoters include the cauliflower mosaic virus (CaMV) 35S transcription initiation region, the 1'- or 2'-promoter derived from T-DNA of *Agrobacterium tumefaciens*, the actin promoter, the ubiquitin promoter, the histone H2B promoter (Nakaysma et al., 1992, *FEBS Lett* 30:167-170), the Smas promoter, the cinnamyl alcohol dehydrogenase promoter (U.S. Pat. No. 5,683,439), the Nos promoter, the pEmu promoter, the rubiseo promoter, the GRP1-8 promoter, and other transcription initiation regions from various plant genes known in the art.

Examples of inducible promoters are the Adh1 promoter which is inducible by hypoxia or cold stress, the Hsp70 promoter which is inducible by heat stress, the PPDK promoter which is inducible by light, the In2 promoter which is safener induced, the ERE promoter which is estrogen induced and the Pepearboxyiase promoter which is light induced.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Relna, M., Puigdomenech, P. and Palau, J.; Isolation and sequencing of a 28 kD glutelin-2 gene from maize: Common elements in the 5' flanking regions among zein and glutei in genes; *Plant Sci.* 47:95-102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res*, 18(21):6426 (1990). See the following site relating to the waxy promoter: Kloesgen, R. B., Gieri, A., Schwarz-Sommer, Z. S. and Saedler, H., Molecular analysis of the waxy locus of *Zea mays, Mol. Gen. Genet.* 203:237-244 (1986). The disclosures of each of these are incorporated herein by reference. The barley or maize Nuc1 promoter, the maize Cim 1 promoter or the maize LTF2 promoter can be used to preferentially express in the nuceilus. See for example U.S. Ser. No. 60/097, 233 filed Aug. 20, 1998 the disclosure of which is incorporated herein by reference.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

The termination region is optional and may be native with the transcriptional initiation region, may be native with theoperahly linked DNA sequence of interest, or may be derived from another source. Convenient termination regions are available from the potato proteinase inhibitor (Pinll) gene or the Ti-plasmid of *A. tumefaciens*, such as the octopine synthase and nopaline synthase termination regions. See also Guerineau et al. (1991) *Mol. Gen. Genet.* 282:141-144; Proudfoot (1991) *Cell* 64:871-674; Sanfacon et al (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639. The disclosures of the above are herein incorporated by reference.

The expression cassettes may additionally contain 5' leader sequences in the expression cassette construct. Such leader sequences can act to enhance translation. Translation leaders are known in the art and include: picomavirus leaders, for example, EMCV leader (Encephalomyocarditis 5' noncoding region) (Elroy-Stein et al. (1989) *PNAS USA* 86:6126-8130); potyvirus leaders, for example, TEV leader (Tobacco Etch Virus) (Allison et al, (1986); MDMV leader ( Maize Dwarf Mosaic Virus); *Virology* 154:9-20), and human immunoglobulin heavy-chain binding protein (BiP), (Macejak et al. (1991) *Nature* 353:90-94); untranslated leader from the coat protein mRNA of alfalfa mosaic virus (AMV RNA 4) (Jobling et al. (1987) *Nature* 325:822-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See. also, Della-Cioppa et al (1987) *Plant Physiol.* 84:985-968. The disclosures of the above are herein incorporated by reference. Other methods known to enhance translation can also be utilized, for example, introns, and the like.

In preparing the expression cassette, the various DMA fragments may be manipulated, so as to provide for the DMA sequences in the proper orientation and, as appropriate, in the proper reading frame. Toward this end, adapters or linkers may be employed to join the DMA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Once the appropriate plant ceils are produced, the nucleotide sequences of interest can be introduced into the plant cells by any method known in the art. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant ceils and subsequent Insertion into the plant genome include microinjection (Crossway et al. (1986) *Biotechniques* 4:320-334), electroporation (Riggs et al. (1986) *Proc. Natl. Acad. Sci. USA* 83:5802-5808, *Agrobacterium*-mediated transformation (Townsend et al., U.S. Pat No. 5,563,055), direct gene transfer (Paszkowski et al. (1984) *EMBO J.* 3:2717-2722), and ballistic particle acceleration (see, for example, Sanford et al., U.S. Pat. No. 4,945,050; Tomes et al. (1995) "Direct DNA Transfer into intact Plant Cells via Microprojectile Bombardment," in *Plant Cell, Tissue, and Organ Culture: Fundamental Methods*, ed. Garnborg and Phillips (Springer-Verlag, Berlin); and McCabe et al, (1988) *Biotechnology* 6:923-926), Also see Weissinger et al. (1988) *Ann. Rev. Genet.* 22:421-477; Sanford et al. (1937) *Particulate Science and Technology* 5:27-37 (onion); Christou et al. (1988) *Plant Physiol.* 87:671-874 (soybean); McCabe et al. (1988) *Bio/Technology* 6:923-926 (soybean): Finer and McMullen (1991) in *Vitro Cell Dev. Biol.* 27P:175-182: (soybean); Singh et al. (1996) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising at al., U.S. Pat. Nos. 5,322783 and 5,324,848; Tomes et al. (1995) "Direct DMA Transfer into intact Plant Dells via Microprojectile Bombardment," in *Plant Cell. Tissue, and Organ Culture: Fundamental Methods*, ed. Gamborg (Springer-Verlag, Berlin) (maize); Klein et: at (1988) *Plant Physiol.* 91:440-444 (maize); Fromm et al. (1990) *Biotechnology* 8:833-839 (maize); Hooykaas-Van Slogteren et al. (1984) *Nature (London)* 311;783-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) Theor. Appl. Genet. 84:560-566 (whisker-mediated transformation); D'Halluin et al. (1992) *Plant Cell* 4:1496-1505 (electroporation); Li et al. (1993) *Plant Cell Reports* 12:250-255 and Christen and Ford (1995) *Annals of Botany* 75:407-413 (rice); Ishida et al. (1996) *Nature Biotechnology* 14:745-750; U.S. Pat. Nos. 5,731,179; 5,591,616; 5,641,664; and 5,981,840 ( maize via *Agrobacterium tumefaciens*); the disclosures of which are herein incorporated by reference.

In planta Agrobacterium transformation is disclosed in the following: Bechtold, N., J. Ellis, G. Peiletier (1993) C. R., *Acad Sci Paris Life Sci* 316:1194-1199; Bechtold, N., B. et al. (2000) *Genetics* 155:1875-1887: Bechtold, H. and G. Pelletier (1998) *Methods Mol Biol.* 82:259-266; Chowrira, G. M., V. Akella, and P. F. Lurguin. (1995) *Mol. Biotechnol.* 3:17-23; Clough, S. J., and A. F. Bent. (1998) Plant J, 16:735-743; Desfeux, C., S. J. Clough, and A. F. Bent. (2000) *Plant Physiol.* 123; 395-904; Peldmann, K. A., and M. D. Marks, (1987) *Mol. Gen. Genet.* 208:1-9; Hu C.-Y., and L. Wang. (1999) In Vitro Cell Dev. Biol.-Plant 35:417-420; Katavic, V. G. W. Haughn, D. Reed, M. Martin, L. Kunsi (1994) *Mol. Gen. Genet.* 245:363-370; Liu, F., et al. (1998) Acta Hort 467:187-192; Mysore, K. S., C. T. Kumar, and S. B. Gelvin. (2000) Plant J. 21:9-18; Touraev, A., E. Stoger, V. Voronin, and E. Heberle-Bors. (1997) Plant J. 12:949-956; Trieu, A. T. et al. (2000) *Plant J.* 22:531-541; Ye, G. N. at al. (1999) *Plant J.* 19:249-257; Zhang, J U. et al. (2000) *Chem Biol.* 7:611-621. The disclosures of the above are herein incorporated by reference, Various types of plant tissue can be used for transformation such as embryo cells, meristematic ceils, leaf cells, or callus cells derived from embryo, leaf or meristematic cells. However, any transformation-competent cell or tissue can be used. Various methods for increasing transformation frequency may also be employed. Such methods are disclosed in WO 99/61619: WO 00/17384; WO 00/28056: WO 00/37645; U.S. Ser. No. 09/498,444; WO 00/50614; U.S. Ser. No. 01/44038; and WO 02/04649, The disclosures of the above are herein incorporated by reference.

The transformed ceils can be contacted with a chromosome doubling agent such as colchicine, anti-microtubule herbicide, or nitrous oxide in an amount sufficient to produce a doubled haploid cell. The transformed cell can foe contacted with the doubling agent before, during, or after the plant regeneration step. Haploid seeds and seedlings produced by the seeds can also be treated with the doubling agent.

Once the DNA sequence of interest has been introduced into tissue from the plant, transformed cells are selected and transgenic plants regenerated using methods well known in the art, See, for example, McCormick et al, (1936) *Plant Cell Reports* 5:81-84; and U.S. Pat. No. 5,981,840, Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, Gordon-Kamm et al., *The Plant Cell* 2:603-613 (1990). Other methods of regenerating plants can be achieved as described by Horsch et al., *Science* 227:1229-1231 (1985) and Fraiey at al, *Proc. Natl. Acad. Sci. U.S.A.* 80:4803 (1083). This procedure typically produces shoots within-two to four weeks and these transformant shoots are then transferred to an appropriate root-inducing medium containing the selective agent and an antibiotic to prevent bacterial growth. The disclosures of the above are herein incorporated by reference.

Regeneration can also be obtained from plant callus, explants, organs, or parts thereof. Such regeneration techniques are described generally in Klee et al., *Ann. Rev. of Plant Phys.* 38:467-486 (1987), The regeneration of plants from either single plant protoplasts or various explants is well known in the art. See. for example, Methods for Plant Molecular Biology, A, Weissbach and H, Weissbach, eds., Academic Press, inc., San Diego, Calif. (1988). For maize cell culture and regeneration see generally, The Maize Handbook, Freeling and Walbot Eds., Springer, New York (1994); Corn and Corn Improvement, 3rd edition, Sprague and Dudley Eds., American Society of Agronomy, Madison, Wis. (1988). The disclosures of the above are herein incorporated by reference.

These regenerated transgenic plants may then be grown to maturity and sexually crossed with the same transformed strain ("selfed"), or "backcrossed" with another plant chosen to obtain transgenic plants having desired characteristics. Alternatively, the regenerated transgenic plants may be used to "introgress" the nucleotide sequence of interest into another genetic line of the same plant species or into a genetic line of another closely related plant species, All publications and patent applications mentioned in this specification are herein incorporated by reference to the same extent as if each individual publication or patent application was specifically and individually indicated to be incorporated by reference.

The following examples are offered by way of illustration and not by way of limitation.

EXAMPLES

Example 1

Transformation and Regeneration of Transgenic Maize Plants

Seeds from any maize genotype are planted and the resulting plants are used as female parent plants (pollen receivers). Seeds from haploid inducer lines, such as Stock 6, RWS, KEMS, KMS or ZMS, are planted and the resulting plants are used as male parent plants (pollen donors). The ears of the female parent plants are shoot-bagged before silk emergence. The silks of the ears on the plants of the female parent plants are pollinated with viable pollen grains collected from the anthers of the male parent plants (haploid inducer plants). This pollination is controlled by the method used regularly in maize breeding program to avoid any foreign pollen contamination. The pollination method results in the production of a frequency of about 5-12% of haploid embryos in each ear. At 4 to 20 days, preferred at 6-15 days and more preferred at 8-13 days and most preferred at 9-11 days after pollination, the immature ears are harvested for transformation purpose. The haploid embryos are isolated based on the identification of the visible marker gene in the inducer lines. For example, if the inducer contains a GFP gene or CRC gene driven by a promoter that allows the GFP or CRC gene expression only in the embryos at the early developmental stage. Typical promoters that are useful include the maize oleosin promoter or maize Lec1 promoter etc, The haploid produced by this system is a maternal haploid that has only one set of chromosomes from the female parent in the embryo cells and has 3 sets of chromosomes in the endosperm cells, two of them from female parent and one of them from male parent. If the inducer line has a visible marker gene, such as GFP or ORG, this marker gene will be included in the endosperm cells only, but not in the embryo cells in the haploid kernels. By using this kind of visible marker, haploid embryos can be identified easily and can be isolated by recognizing either the GFP negative or CRC negative embryos.

Haploid maize embryos from greenhouse or field grown plants are bombarded with a plasmid containing a gene of interest. The maize embryos are isolated from ears 9-11 days after pollination using a scalpel. The ears are surface sterilized in 30% Clorox bleach plus 0.5% Micro detergent for 20 minutes, and rinsed two times with sterile water. The embryos are excised and placed embryo axis side down (scutellum side up), 25 embryos per plate, on 560Y medium for 4 hours and then aligned within the 2,5-cm target zone in preparation for bombardment.

A plasmid vector comprising a polynucleotide of interest operably linked to a selected promoter is made. This plasmid DNA plus plasmid DNA containing a PAT selectable marker is precipitated onto 1.1 µm (average diameter) tungsten pellets using a CaCl2 precipitation procedure as follows; 100 µl prepared tungsten particles in water, 10 µl (1 µg) DMA in TrisEDTA buffer (1 µg total), 100µl 2.5 M $CaCl_2$, 10 µl 0.1 M spermidine.

Each reagent is added sequentially to the tungsten particle suspension, while maintained on the multitude vortexer. The final mixture is sonicated briefly and allowed to incubate under constant vortexing for 10 minutes. After the precipitation period, the tubes are centrifuged briefly, liquid removed, washed with 500 µl 100% ethanol and centrifuged for 30 seconds. Again the liquid is removed, and 105 µl 100% ethanol is added to the final tungsten particle pellet. For particle gun bombardment, the tungsten/DMA particles are briefly sonicated and 10 µl spotted onto the center of each macrocarrier and allowed to dry about 2 minutes before bombardment. The sample plates are bombarded at level #4 in particle gun #HE34-1 or #HE34-2. All samples receive a single shot at 650 PSI, with a total often aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.8 gallon) and grown to maturity. Plants are monitored and scored for the genotype and/or phenotype of interest.

Bombardment medium (580Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I H2O following adjustment to pH 5,8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Embryo-derived callus tissue is cultured on selection medium for about 2-3 months. Putative stable transformed callus can be identified based on the callus growth on herbicide-containing selection medium. Chromosome doubling can be performed at this stage or at the beginning of plant regeneration. Chromosome doubling agents, such as colchicine (0.01%-0.2%) or APM (5-225 μM) or Pronamide (0,5-20 μM) are added to either callus selection medium (560R) or plant regeneration medium (288J), Callus tissue is maintained on those media for 1 to a few days and the samples of the treated calli are examined periodically to confirm chromosome doubling. In the alternative, the callus tissue can be maintained in a chamber or a container in which $N_2O$ (nitrous oxide) is provided at 2-12 atmospheres for a few hours to a few days. Callus samples are examined to confirm chromosome doubling. Regular plant regeneration procedures are used following chromosome doubling.

Plant regeneration medium (288J) comprises 4.3 g/l MS salts (GIBCO 11117-074), 5.0 ml/l MS vitamins stock solution (0,100 g nicotinic acid, 0.02 g/l thiamine HCL, 0.10 g/l pyridoxine HCL, and 0.40 g/l glycine brought to volume with polished D-I H2O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H2O after adjusting to pH 5.8); 3,0 g/l Geirite (added after bringing to volume with D-I H2O); and 1.0 mg/l indoieacefic acid and 3,0 mg/l blalaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HGL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 6 g/l baeto-agar (added after bringing to volume with polished D-I H2O), sterilized and cooled to 60° C.

Chromosomal doubling can also be performed in the regenerated plants, haploid seeds or the haploid seedlings germinated from haploid seeds. Similar doubling agents can be applied to these expiants, RepA can be used to increase chromosomal doubling efficiency. Haploid plant tissues (callus, seeds, seedlings etc.) containing the RepA polynucleotide are used in chromosomal doubling with the methods described above. The frequency of doubled haploids is increased several fold.

RepA containing materials are compared with non-RepA materials for chromosomal doubling efficiency in corn haploid plants. Both types of materials are grown in the same condition at the same time. However, the haploid plants that contain RepA polynucleotide exhibit 60% chromosomal doubling frequency versus non-RepA haploid plants which exhibit 26% chromosomal doubling frequency. The RepA containing doubled haploid plants produced 28 kernels per plants on the average and the non-RepA doubled plants have produced 23 kernels per plants on the average.

Example 2

*Agrobacterium*-mediated Transformation of Maize

For *Agrobacterium*-mediated transformation of maize the method of Zhao is employed essentially as described in U.S. Pat. No. 5,981,840, the contents of which are hereby incorporated by reference. Haploid embryos (preferably about 7-13 days after pollination) are isolated from maize and the embryos are contacted with a suspension of *Agrobacterium*, where the bacteria are capable of transferring the nucleotide sequence(s) of interest to at least one cell of at least one of the embryos, in this step the embryos are typically immersed in an *Agrobacterium* suspension for the initiation of inoculation, Preferably, the *Agrobacterium* suspension contains 100 μM acetosyringone. The embryos are co-cultured for a time with the *Agrobacterium*.

Generally the embryos are cultured on solid medium following the infection step. Following this co-cultivation period an optional "resting" step lasting 6-7 days is contemplated. In this resting step, the embryos are incubated in the presence of at least one antibiotic known to inhibit the growth of *Agrobacterium* without the addition of a selective agent for plant transformants. Next, inoculated embryos are cultured on solid medium containing a selective agent and growing transformed callus is recovered, The callus is then regenerated into plants, and calli grown on selective medium are cultured on solid medium to regenerate the plants.

Haploid immature embryos were isolated from maize Hi-II immature ears that were pollinated with haploid inducer line RWS. These embryos were as transformed by the method described in US Pat. No. 5,981,840. Hi-II immature ears pollinated with haploid inducer line RWS contain both diploid embryos (averaged ~87%) and haploid embryos (averaged ~13%), A marker gene was used that expressed at early stage of immature embryos (8-14 days after pollination) in the haploid inducer line RWS to identify haploid immature embryos in Hi-II ears. Stably transformed haploid embryos can be confirmed either by the transgene expression in the transformed callus, regenerated plants and seeds etc. or by molecular analysis, such as PGR, Southern blots and Northern blots etc. The data from 6 experiments are listed in Table 1 to demonstrate the capability to transform haploid expiants. The following constructs were used for the transformation.

Ubi:GFP:pinll and 35S:Bar:pinll were used for experiments 1,2, and 5, Nos:Lec1:pinll and Ubi:MO-PAT::GFP:pinll were used in experiments 3, 4, and 6.

TABLE 1

Transformation of Maize Hi-II Haploid Embryos

| Experiment No. | Total embryo No. | Total haploid embryos | Transformed haploid embryos | Frequency of haploid transformation |
|---|---|---|---|---|
| 1 | 108 | 14 | 3 | 21% |
| 2 | 84 | 11 | 2 | 18% |
| 3 | 32 | 4 | 1 | 25% |
| 4 | 93 | 12 | 6 | 50% |
| 5 | 95 | 12 | 5 | 42% |
| 6 | 120 | 16 | 7 | 44% |
| Sum | 532 | 69 | 24 | 35% |

The method of chromosome doubling is essentially the same as for Example 1. The media used in plant regeneration is disclosed in U.S. Pat. No. 5,981,840.

Example 3

Transformation of Meristematic Tissue from Haploid Seeds

Transformation of meristematic tissue is disclosed in U.S. Pat. No. 5,736,369. The method comprises particle bombardment of meristem tissue at a very early stage of development and the selective enhancement of transgenic sectors toward genetic homogeneity in cell layers that contribute to germline transmission. Embryos are obtained as described in Example 1 and incubated on maturation medium. The apical dome of several embryos is disrupted prior to bombardment to force the meristem to reorganize and form new meristematic areas. Mechanical disruption is performed by means of micromanipulation needles. Embryos are maintained in the dark at 28° C. for seven days on maturation medium and then transferred to 272K medium containing 150 mg/L Tobramycin sulfate. The embryos will have multiple meristem formation with elongated cotyledons. The embryos are then incubated in light at 28° C. A chromosome doubling agent is used at the initiative stage of the novel meristems to double chromosomes of the resulting transformed plants.

Example 4

Transformation of Somatic Tissue Derived from Haploid Seeds

Fertile plants have been developed from the leaf segments in a number of monocot species such as Orchard grass (Manning and Conger 1982, *Theor. Appl. Genet.* 63:155-159; Conger et ah 1983, *Science* 221:850-851; Trigiano, et al. 1989, Bot. Gaz. 150:72-77), Maize (Chang, 1983, *Plant Cell Reports* 2:183-185; Conger et al. 1987, *Plant Cell Reports* 6:345-347; Wenzler and Mains 1986, Protoplasma 131:103-105; Debjani Sinha Ray and Ghosh 1990, *Annals of Botany* 66:497-500; Doiezelova et al. 1992, *Plant Cell Tissue and Organ Culture* 31:215-221), Oat (Chen et al. 1995, *Plant Cell Reports* 14:354-358; Chen et al. 1895, *Plant Cell Reports* 14:393-397), Sorghum (Wemocke and Brettel 1980, *nature* 287:138-139; Wernicke et al 1982, Protolasma 111 ;53-82), and Wheat (Ahuja et al. 1982, Z. Pflanzenzuchtg 89:145-157).

Somatic tissues derived from seeds have been used for genetic transformation by both particle gun bombardment and Agrobaeterium. Zarate et al. (1999, *Biotechnology Lettes* 21:997-1002) obtained stable transformation via bombardment of *Catharathus roseus* plants through adventitious organogenesis of buds isolated from germinated seeds. Zhong et al, (1996, *Plant Physiol.* 110:1097-1107) and U.S. Pat. No. 5,767,368 (issued Jun. 16, 1998) disclosed the method of transformation of maize by bombarding meristem primordia which are derived from shoot apices. Reichert (U.S. Pat. No. 6,140,555, issued Oct. 31, 2000) transformed nodal explants derived from germinated seeds by bombardment, Mahalakshml-Akella and Khurana-Paramji disclosed *Agrobacterium*-mediated transformation of various tissues derived from mature seeds, such as leaf base, seedling and mature seeds in wheat (1996, *Journal of Plant Biochemistry and Biotechnology* 4:55-50). Methods described in Example 1 and 3 are used for chromosome doubling.

Example 5

Identifying Haploids

Haploid ceils, embryos, callus, plants etc. are identified with several methods, such as, by using Flow Cytometer to identify ploidy for all tissues, by chromosomal counting to identify ploidy for ail tissues that provide dividing ceils, and by measuring the length of guard ceils or counting the chloroplast numbers in guard cells of plant leaf tissues. Guard cells provide an easy and quick tool for ploidy assay at the plant stage.

Example 6

Screening of Transgenic Events

Transgenic plants are produced as described above. Because the resulting transgenic events/plants are homozygous, all of the genes including dominant and recessive genes are expressed in the plants. Carefully evaluating the expression profile of the gene of interest and the interaction of the gene with the whole genome at an early generation (T0 and/or T1) will allow researchers to discard unnecessary events and focus on the candidate events at an early stage, if these doubted haploid lines are suitable for hybrid formation they can be used directly in hybrid yield testing as top crosses or as putative final products.

Example 7

Transforming an Inducer Line with a Marker Gene to Identify Haploid Immature Embryos at Early Stage Haploid inducer lines, such as RWS, KEMS, ZMS or KMS, do not have a marker gene that can be expressed in the early embryo development stage, such as 8-12 days after pollination. However, transforming embryos in most plants, such as corn, sorghum, wheat, barley and rice etc, usually requires embryos at an early development stage. The marker gene(s) used in the current inducer lines does not express well at early embryo development stage. To identify haploid immature embryos at the beginning of transformation process is useful to the efficient development of new technology for haploid transformation or to modify the existing technology to favor haploid targets.

The Lec1 promoter can provide expression during early embryo development and during the callus stage of plant regeneration. The lec1 promoter is described in U.S. PCT application No., U.S. Ser. No. 01/44732 filed Nov. 20, 2001, the disclosure of which is incorporated herein by reference.

An inducer line, such as RWS in corn, is transformed with the Led promoter driving a marker gene, such as GPP, YFP, CFP or CRC etc. This inducer line is used as the male parent to pollinate any other genotypes of corn plants. The resulting ears contain both haploid and diploid kernels. The Led promoter is an early active promoter in immature embryos. The gene driven by the Led promoter can be expressed as early as 7 days after pollination and can last until 15 days after pollination. In addition, the gene driven by the Led promoter is expressed only in the embryos, and not in the endosperm. The haploid kernels derived from a genotype pollinated by the inducer line contain the inducer genomic set in their endosperm only, but not in their embryos. On the other hand, the diploid kernels from this cross contain the inducer genomic set in both the embryo and the endosperm. The resulting haploid embryos do not contain the marker gene and the diploid embryos do contain the marker gene. In this way the haploid embryos can be easily identified at the beginning of transformation. Also, any marker gene used in the inducer line transformation will not be present in the haploid embryos and will not affect the resulting doubled haploid transformants.

Example 8

Transforming an Inducer Line with an Inducible Seed Lethal Gene

In the present invention haploid inducer lines, such as RWS, KEMS, ZUS or KMS, can be transformed with a lethal gene that is expressed specifically in embryos of the mature seeds. The expression of the lethal gene is controlled with an inducible system. Because the expression of the lethal gene is controlled by an inducible promoter, it cannot express in the inducer lines when the inducing agent is not present. The seeds of the inducer lines can be germinated as normal seeds. After crossing the inducer line and the female parent the embryos of all the diploid seeds contain the inducible lethal gene, but the embryos of the haploid seeds do not contain the lethal gene. By inducing the expression of the lethal gene when the F1 seeds germinate, the diploid F1 seeds cannot germinate due to expression of the lethal gene in their embryos. However, all of the haploid seeds can germinate normally because they do not contain the lethal gene in their embryos. Ali of the germinating seedlings are haploid.

The plant cell is transformed with a DMA sequence whose expression is lethal to the plant cell and an inducible promoter which contains a receptor binding site. When the receptor binds to the binding site, the promoter is functional and results in the expression of the lethal gene. The plant cell is also transformed with a second DNA sequence whose expression produces a precursor of the receptor which can interact with an external agent to form a functional receptor. The functional receptor then binds to the receptor binding site to induce the expression of the lethal gene.

An alternative way to induce the expression of a lethal gene is by transforming a lethal gene info a plant cell, wherein the expression of the lethal gene is controlled by a plant-active promoter. The lethal gene and the promoter are linked to each other, but separated by a blocking sequence that is flanked by specific excision sequences. The presence of the blocking sequence prevents the expression of the lethal gene in the plant cell. The plant cell is also transformed with a second gene that encodes a recombinase specific for the excision sequences flanking the blocking sequence of the lethal gene. The second gene is operably linked to an inducible promoter that contains a receptor binding site. When the receptor binds to the binding site, the promoter is functional and results in the expression of the recombinase. The plant cell is transformed with a third gene whose expression produces the precursor of the receptor that can interact with an external agent to form a functional receptor. The functional receptor binds to the binding site to produce expression of the recombinase. Expression of the recombinase results in excision of the blocking sequence between the plant-active promoter and the lethal gene and results in expression of the lethal gene in the plant cell. In this case, if the inducible promoter is not 100% tightly-induced by adding the external agent, the promoter leaks at a low level which is not sufficient to induce recombinase activity, it should not be lethal to the plant cell.

A third method to produce an inducible system comprises transforming a lethal gene into a plant cell, The expression of the lethal gene is controlled by an inducible promoter. The lethal gene and the inducible promoter are linked to each other, but separated by a blocking sequence that is flanked by specific excision .sequences. The presence of the blocking sequence prevents the expression of the lethal gene in the plant cell. The plant cell is also transformed with a second gene that encodes a recombinase specific for the specific excision sequences flanking the blocking sequences of the lethal gene and a second inducible promoter that contains a receptor binding site, induction of the second inducible promoter is different from the first inducible promoter as different inducing agents are used. When the receptor binds to the binding site, the promoter is functional and results in the expression of me recombinase. The plant cell is transformed with a third gene whose expression produces a precursor of the receptor that can interact with an external agent to form a functional receptor and the functional receptor binds to the binding site to cause expression of the recombinase. The expression of the recombinase results in the excision of me blocking sequence between the first inducible promoter and the lethal gene and by adding the appropriate inducing agent to induce this promoter function, the lethal gene can be expressed in the plant cell. In this case, if both inducible promoters are not 100% tightly-induced by adding the external agent, the effect of the promoter leaking will be significantly diluted.

In the above methods, the inducing agent can be mixed with a seed coating mix for F1 seeds. After planting the seeds in the field, the diploid seeds cannot germinate due to the induction of the expression of the lethal gene.

A typical inducible receptor binding sequence is ERE (Estrogen Responsive Element) (Klein-Hitpass et al. 1980, *Nucleic Acids Res*, 18:647-663; Bruce et al. 2000, *The Plant Cell*, 12:85-79). Typical inducing agents are estradiols (β-estradiol-17-[β-D-glucuronide] or β-estradiol-3-[β-D-glucuronide] or 17α-ethylnylestradiol for ERE) or safener for CAS.

Typical inducible promoters are In-2 promoter (Hershey et al. WO 9011361) and tetracycline-inducible promoter (Bellingcampi et al., 1996, *Plant Cell* 8:477-437; De-Veylder-Lieven et al., 2000, *Journal of Experimental Botany* 51:1647-1853), and typical inducing agents are safener (for In-2 promoter) and tetracycline.

Typical lethal genes are DAM (DAM Methylase gene) or RIP (ribosomal Inhibitor protein gene). Typical embryo specific promoters are gib-1 or Oleosin. Typical recombinase genes are FLP and ORE and typical flanking sequences are to FRT and LOX.

Example 9

Providing a Growth-stimulating Gene Increases the Frequency of Haploid Embryos after Crossing the Inducer-line to any Maize Genotype There are two variations on this method.

A. In the first, the genotype of interest (i.e. PHN46) is transformed with a growth-stimulating polynucleotide (GS) operably linked to a promoter that drives expression in the embryo. For example, a cassette containing LTP2::LEC1::pinII is introduced into PHN46. T0 plants are regenerated and are selfed to produce seed that are LEC1/LEC1 homozygous. These seed are germinated, the plants grown to maturity, and pollinated with the haploid-inducar line. For comparison, wild-type (non-transformed) PHN46 seed is also planted and pollinated with the haploid inducer. For ears on wild type FHN46 plants, the frequency of kernels containing haploid embryos ranges between 5-10%, For ears developing on LEC1/LEC1 PHM46 plants, the frequency of kernels that contain haploid embryos is expected to be higher, for example ranging between 10-20%, B. In the second variation on this method, the inducer line is transformed with an expression cassette containing an endosperm-specific promoter, a GS gene, and an endosperm-specific 3' sequence. For example, GZ::PSK::GZ is transformed into the haploid-inducar line. Plants are regenerated and selfed to produce PSK/PSK homozygous seed, The PSK/PSK haploid-inducer seed is planted, grown to maturity and used to pollinate ears from PHN46. For comparison, non-transgenic haploid-inducer seeds are also planted, and the resultant plants used to pollinate ears from PHN46. For PHN46 ears pollinated with non-transgenic haploid-inducer pollen, the frequency of kernels containing haploid embryos ranges between 5-10%. For PHN46 ears pollinated using pollen from transgenic PSK/PSK haploid-inducer plants, the frequency of kernels that contain haploid embryos is expected to be higher, for example ranging between 10-20%.

Example 10

Providing a Growth-stimulating Gene Increases the Frequency of Haploid Embryo Transformation Again, there are two variations on this method, A. In the first, any given genotype (i.e. PHM46) is transformed with a growth-stimulating (GS) gene operably linked a promoter that drives expression in the embryo. For example, a cassette containing Lec1::RepA::Lec1 is introduced into PHN46. T0 plants are regenerated and selfed to produce seed that are RepA/RepA homozygous. These seed are germinated, the plants grown to maturity, and pollinated with the haploid-inducer line. For comparison, wild-type (non-transformed) PHN46 seed is also planted and pollinated with the haploid inducer. For PHM48 RepA/RepA transgenic ears pollinated with haploid-inducer pollen, the *Agrobacterium*-mediated transformation frequency is expected to fall in the range between 8-20%, For wild type non-transformed PHN46 ears pollinated using the haploid-inducer line, the *Agrobacterium*-mediated transformation frequency ranges between 2-4%.

B. in the second variation on this method, the inducer line is transformed with an expression cassette containing an endosperm-specific promoter, a GS gene, and an endosperm-specific 3' sequence. For example, GZ::PSK::GZ is transformed into the haploid-inducer line (the GZ promoter is disclosed in Ueda et al. (1994) *Mol. Cell Biol* 14(7):4350-4359). Plants are regenerated and selfed to produce PSK/PSK homozygous seed. The PSK/PSK haploid-inducer seed is planted, grown to maturity and used to pollinate ears from PHN46. For comparison, non-transgenic haploid-inducer seeds are also planted, and the resultant plants used to pollinate ears from PHN46. For PHN46 ears pollinated with non-transgenic haploid-inducer pollen, the *Agrobacterium*-mediated transformation frequency ranges between 2-4%. For PHN46 ears pollinated using pollen from a homozygous transgenic (PSK/PSK) haploid-inducer plant, the *Agrobacterium*-mediated transformation frequency is expected to range-between 8-20%.

Example 11

Providing a Growth-stimulation Gene Increases the Frequency of Chromosome Doubling in Haploid Cells The genotype of interest is transformed with a GS gene, pollinated with the haploid inducer line, and the resultant haploid progeny will have higher chromosome doubling rates (Induced either in the callus stage or in germinating seedlings) relative to non-transformed material from the same genotype.

General note: Examples 9 and 10 could theoretically utilize any of the potential GS genes listed. Example 11 covers either over-expression of GS genes that stimulate the cell cycle such as Cyclin A, Cyclic B, Cyclin C, Cyclin D, Cyclin E, Cyclin P, Cyclin G, and Cyclin H; Pin1; E2F; Cdc25; RepA, or to suppressing activity of cell cycle repressors such as Rb, CKl, prohibitin, or wee1. Suppressing activity could involve antisense, hairpins, sense co-suppression, over-expressing a dominant-negative mutant, expressing antibodies raised against the protein, etc.

What is claimed is:

1. A method of transforming a somatic cell of an isolated maize haploid embryo with a polynucleotide of interest using *Agrobacterium*-mediated transformation and treating the transformed cell with a chromosome doubling agent to produce a transgenic homozygous plant cell, wherein said maize haploid embryo is produced by crossing a selected female parent with a male inducer line.

2. The method of claim 1, wherein a growth stimulation polynucleotide has been introduced into the female parent or male inducer line by stable or transient transformation.

3. The method of claim 2 wherein the growth stimulation polynucleotide encodes RepA or Lec1.

4. The method of claim 1 wherein the male inducer line contains a scorable marker gene operably linked to an embryo-preferred promoter.

5. The method of claim 1 further comprising regenerating a transgenic homozygous plant from the transgenic homozygous plant cell.

6. A method of producing a stably transformed double haploid maize plant comprising:
   a) pollinating a maize plant with pollen from a haploid inducer line, wherein said haploid inducer line comprises a marker gene that is expressed in maize embryos at the early developmental stage,
   b) obtaining maize embryos that are haploid, wherein:
      i. one or more maize kernels resulting from step (a) are identified as containing marker negative embryos, thus identifying haploid maize embryos, and said haploid maize embryos are isolated from the maize kernels; or ii. isolating maize embryos from maize kernels resulting from step (a) and identifying marker negative embryos, thus identifying haploid maize embryos, c) stably transforming a cell of a haploid maize embryo obtained in (b) with a polynucleotide of interest using *Agrobacterium*-mediated transformation to form a transformed maize cell, d) growing transformed callus from the transformed maize cell, e) treating the transformed callus with a chromosome doubling agent to produce a stably transformed double haploid maize cell, and f) regenerating said double haploid maize cell into a double haploid maize plant.

7. The method of claim 6, wherein a growth stimulation polynucleotide has been introduced into the maize plant that is pollinated in step (a) or the haploid inducer line by stable or transient transformation.

8. The method of claim 7 wherein the growth stimulation polynucleotide encodes RepA or Lec1.

* * * * *